US010442237B2

(12) United States Patent
Garcia et al.

(10) Patent No.: US 10,442,237 B2
(45) Date of Patent: Oct. 15, 2019

(54) SHARPENER WITH HEATING ELEMENT

(71) Applicants: Regina M. Garcia, Alhambra, CA (US); Eric R. Garcia, Alhambra, CA (US)

(72) Inventors: Regina M. Garcia, Alhambra, CA (US); Eric R. Garcia, Alhambra, CA (US)

( * ) Notice: Subject to any disclaimer, the term of this patent is extended or adjusted under 35 U.S.C. 154(b) by 227 days.

(21) Appl. No.: 15/687,547

(22) Filed: Aug. 28, 2017

(65) Prior Publication Data

US 2018/0056711 A1 Mar. 1, 2018

Related U.S. Application Data

(60) Provisional application No. 62/380,345, filed on Aug. 26, 2016.

(51) Int. Cl.
*B43L 23/00* (2006.01)
*B43L 23/02* (2006.01)
*A61L 2/04* (2006.01)
*B43L 23/08* (2006.01)

(52) U.S. Cl.
CPC ............... *B43L 23/008* (2013.01); *A61L 2/04* (2013.01); *B43L 23/00* (2013.01); *B43L 23/02* (2013.01); *B43L 23/08* (2013.01)

(58) Field of Classification Search
CPC ...... B43L 23/00; B43L 23/004; B43L 23/008; B43L 23/02; B43L 23/06; B43L 23/08; B43L 23/085
See application file for complete search history.

(56) References Cited

U.S. PATENT DOCUMENTS 4,564,351 A * 1/1986 LaRue .................... B43L 23/00 425/383
5,151,575 A * 9/1992 Lilly .................. B29C 67/0044 156/499
7,472,728 B1 * 1/2009 Geffen .................. B43L 23/008 144/28.5

* cited by examiner

*Primary Examiner* — Matthew Katcoff
(74) *Attorney, Agent, or Firm* — Eric R. Garcia, Esq.

(57) ABSTRACT

A pencil sharpener is disclosed. The pencil sharpener may include a housing and a sharpener assembly disposed within the housing. The sharpener assembly is configured to sharpen an end of a pencil. The pencil sharpener also includes a heating element coupled to the sharpener assembly that is configured to heat the end of the pencil. The pencil sharpener may also include a sanitation element to sanitize the tip of a pencil.

20 Claims, 8 Drawing Sheets

SHARPENER WITH HEATING ELEMENT

CROSS-REFERENCE TO RELATED APPLICATIONS

This application claims priority to U.S. Provisional Patent Application Ser. No. 62/380,345, filed Aug. 26, 2016, the disclosure of which is incorporated herein by reference in its entirety.

FIELD

The present invention generally relates to pencil sharpeners and more particularly to a cosmetic pencil sharpener having an integrated heating element.

BACKGROUND

Conventionally, sharpeners used for cosmetic pencils, such as lipliner, eyeliner or eyebrow pencils, require manual rotation of the cosmetic pencil to sharpen its tip. The resulting sharpened tip is subject to breakage, cracks, or other damage because of the delicate nature of the cosmetic composition which may comprise solid oils, liquid oils, volatile oils, and resins. Some users of cosmetic pencils may resort to heating the tip of a cosmetic pencil using a lighter or some other heat source to soften or stabilize the cosmetic composition after sharpening to prevent breakage and improve applicability. In addition, some users heat the tip of a cosmetic pencil to sterilize or sanitize the cosmetic composition.

SUMMARY

According to various aspects of the subject technology, a pencil sharpener with a heating element is disclosed. In some aspects the sharpener may comprise a base for holding cuttings and debris, a removable cover, a dial having an assortment of different sized openings for accepting different diameter pencils, a sharpener assembly housed within the base, and a heating element thermally coupled to the sharpener assembly configured to heat tips of a pencil inserted within the pencil sharpener.

In other aspects of the subject technology, the pencil sharpener may include a separate heating element accessible via a different opening on the dial that is configured for reheating a tip of a pencil.

In one aspect of the subject technology, the pencil sharpener may include a sanitation element for eliminating bacterial or sterilizing an applicator end or tip of a pencil. The sanitation element may be integrated into the sharpener assembly.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
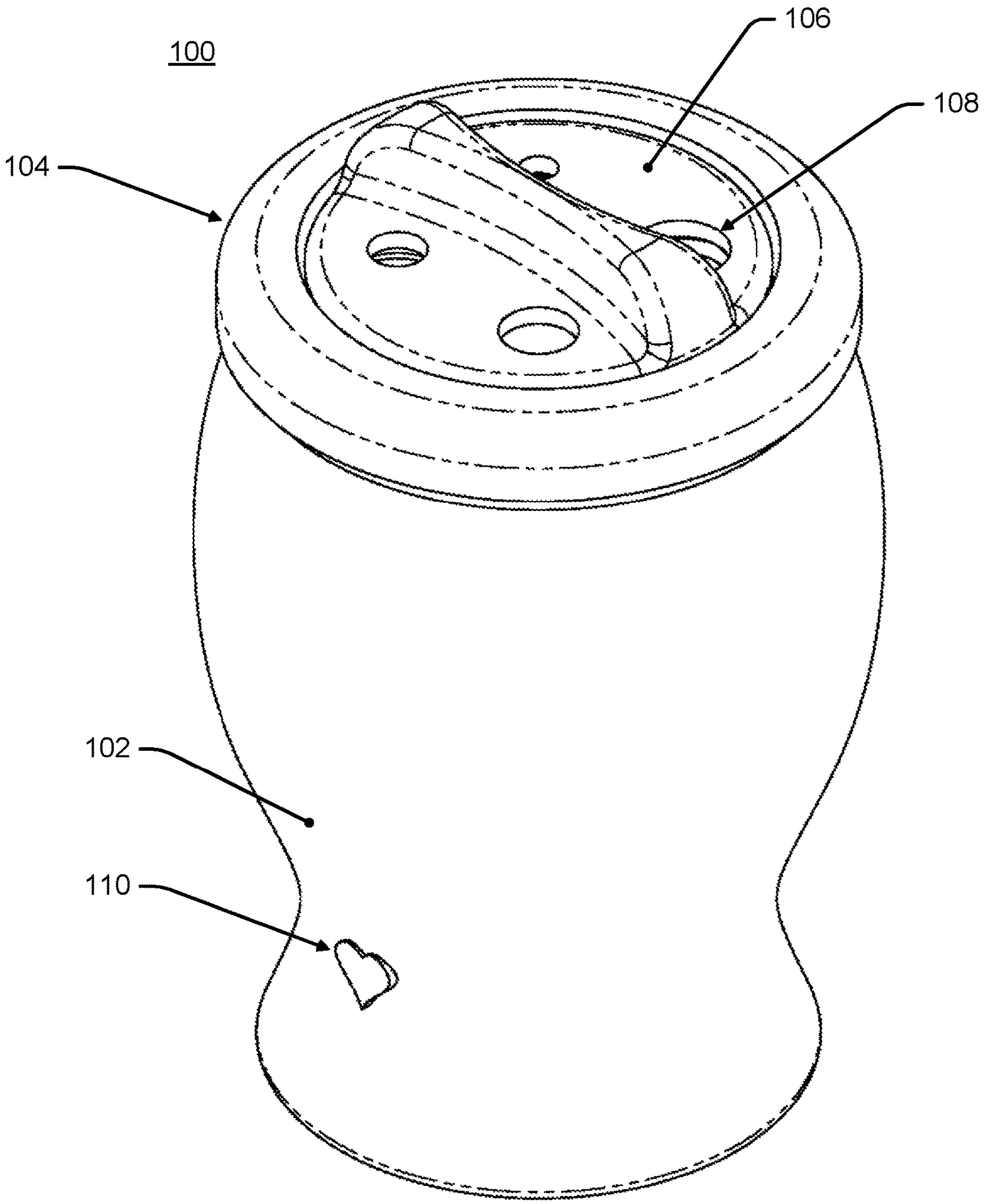
FIG. 1 illustrates a perspective view of a pencil sharpener with an integrated heating element, in accordance with various aspects of the subject technology.

FIG. 1 illustrates a perspective view of a pencil sharpener with an integrated heating element 100, in accordance with various aspects of the subject technology. The sharpener 100 comprises a base 102, lid 104, and dial 106. The base 102 is configured to receive cuttings and other debris resulting from sharpening of pencils. The lid 104 is configured to be removable from the base to allow emptying of any debris collected in the base 102. The lid 104 also comprises a dial 106 that may be rotatably coupled to the lid 104. The dial 106 comprises at least one opening 108 that is configured to receive and accept a pencil, such as a cosmetic pencil including lipliner, eyeliner or eyebrow pencils. Sharpener 100 may also include a power and/or indicator button 110 that is configured to power on and/or off the sharpener 100 upon actuation. Button 110 may also provide a user an indication of the status of the sharpener 100. For example, button 110 may glow a certain color, such as green, to indicate to a user that a heating element 116 (shown in FIG. 4A) has reached adequate temperature and the sharpener is ready to use. The button 110 may glow a different color, such as red, or offer some other indication, such as by blinking, to indicate to the user that the heating element 116 (shown in FIG. 4A) is warming up. Further, button 110 may also indicate to a user that an optional battery 120 (shown in FIG. 4A) requires recharging or changing.

Figure 2A:
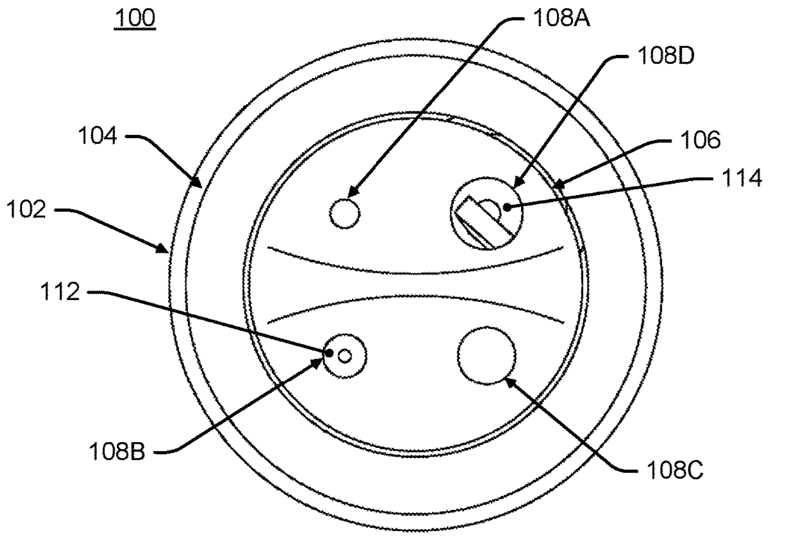
FIG. 2A illustrates a top view of a pencil sharpener with an integrated heating element, in accordance with various aspects of the subject technology.

Referring to FIG. 2A, a top view of the pencil sharpener 100 is shown. Lid 106 may comprise different sized openings 108A-D that are each configured to receive different sized pencils. For example, opening 108A may be configured to receive a small diameter pencil, such as one having a diameter of about 0.25 inches. Opening 108B may be configured to receive a slightly larger sized pencil, such as one having a diameter of 0.38 inches. Opening 108B may be configured to receive a slightly larger sized pencil, such as one having a diameter of about 0.38 inches. Opening 108C may be configured to receive a slightly larger sized pencil, such as one having a diameter of about 0.5 inches. Opening 108D may be configured to receive a slightly larger sized pencil, such as one having a diameter of 0.63 inches. The sizes of openings 108A-D are mere examples and it is understood that a variety of other sizes may be employed without departing from the scope of the invention.

Figure 2B:
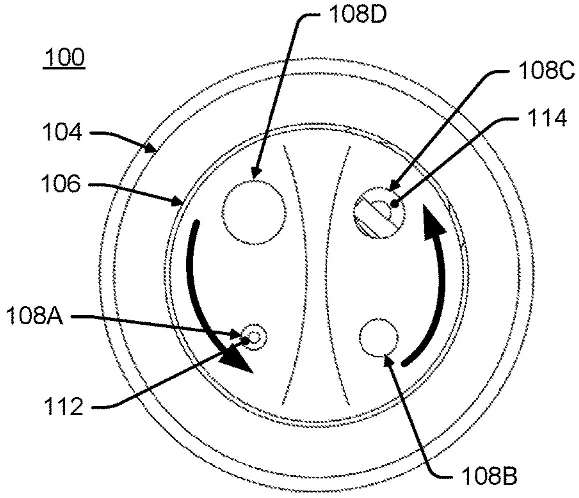
FIG. 2B illustrates another top view of a pencil sharpener with an integrated heating element, in accordance with various aspects of the subject technology.

In one aspect, the lid 106 may be rotated to allow selection of a desired opening 108A-D. For example, FIG. 2A depicts opening 108D selected for sharpening of a pencil and opening 108B selected for heating of a pencil. Should opening 108C be desired for sharpening, the user may rotate lid 106 to align opening 108C with the sharpener assembly 114, as shown in FIG. 2B. Likewise, should opening 108A be desired for heating of a pencil, the lid 106 may be rotated to align opening 108A with the heating element 112, as shown in FIG. 2B. In some aspects, a user may desire to heat a tip of a pencil to soften or stabilize the cosmetic composition to prevent breakage of the pencil tip, improve applicability of the cosmetic composition, and/or to sterilize or sanitize the cosmetic composition.

Figure 2C:
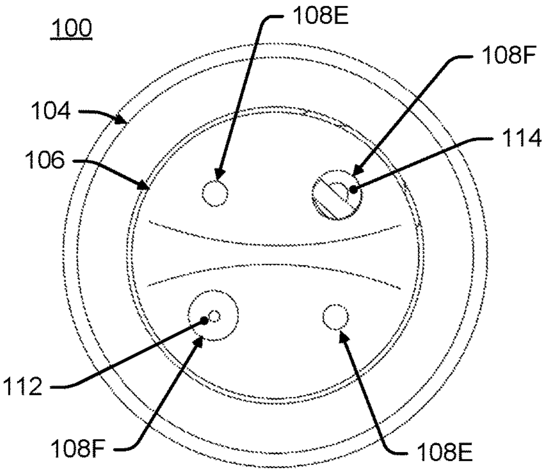
FIG. 2C illustrates another top view of a pencil sharpener with an integrated heating element, in accordance with various aspects of the subject technology.

In another aspect of the subject technology, the lid 106 may be configured with pairs of openings 108E and 108F, as shown in FIG. 2C. Each pair of openings has the same or substantially the same size or diameter. Referring to FIG. 2C, the lid 106 may be configured with a first pair of openings 108E and a second pair of openings 108F. The openings 108E, 108F are configured on the lid 106 such that when a first opening is aligned with the sharpener assembly 114, the corresponding second opening of the pair is aligned with the heater 112. For example, as shown in FIG. 2C, first opening of pair 108F is shown aligned with the sharpener assembly 114 with the second opening of pair 108F also shown aligned with the heater 112. In this configuration, a user may sharpen and heat the same pencil or pencils of similar size without having to rotate lid 106.

Figure 3:
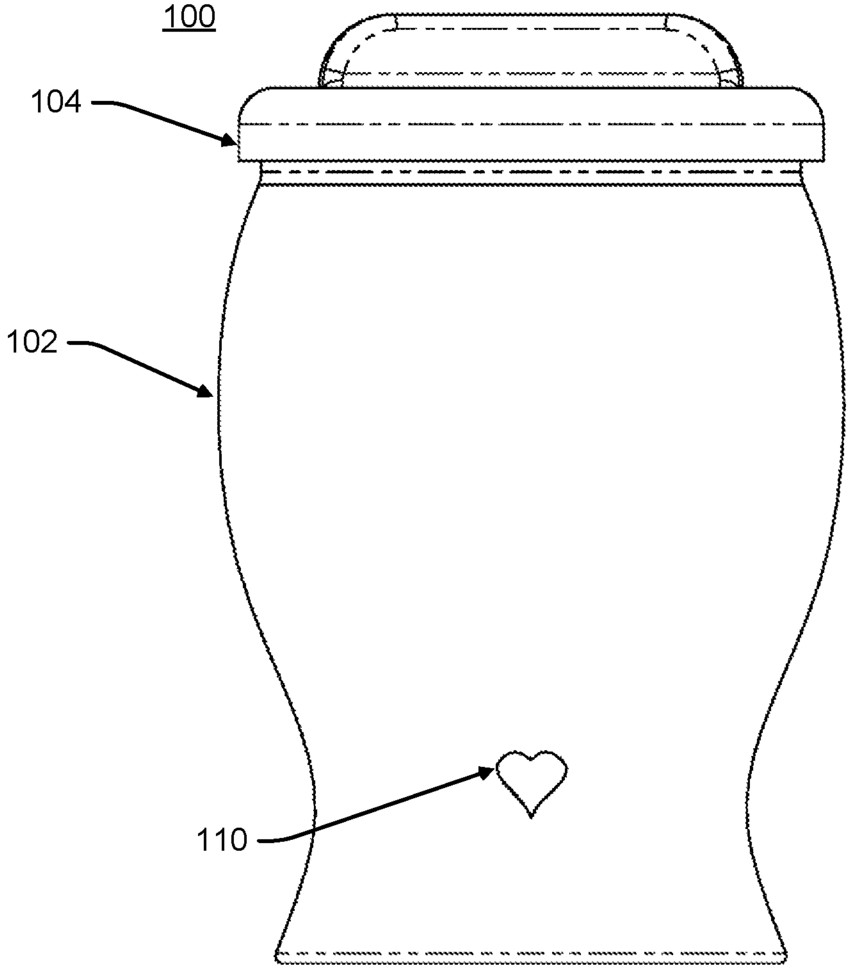
FIG. 3 illustrates a front view of a pencil sharpener with an integrated heating element, in accordance with various aspects of the subject technology.

Referring to FIG. 3, a front view of the sharpener 100 is shown. As discussed above, the sharpener 100 comprises a base 102, removable lid 104 and power button with indicator 110.

Figure 4A:
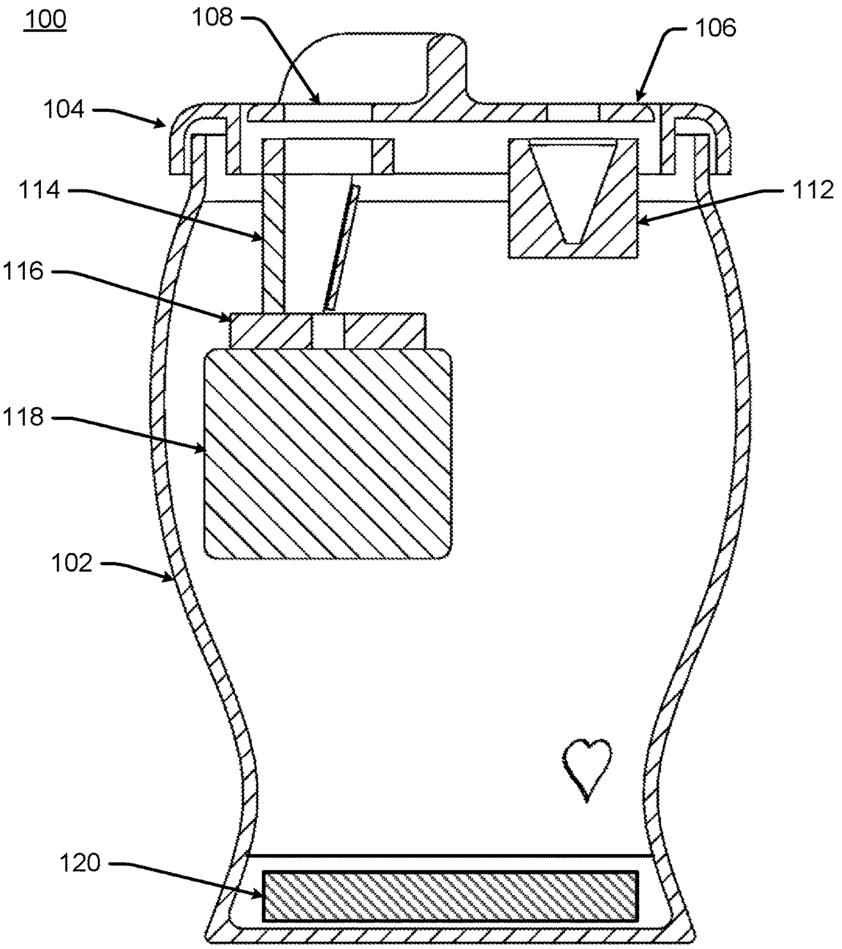
FIG. 4A illustrates a front section view of a pencil sharpener with an integrated heating element, in accordance with various aspects of the subject technology.

Referring to FIG. 4A, a front section view of the sharpener 100 is depicted. The base 102 may house sharpener assembly 114, heating element 116, and motor 118. Sharpener assembly 114 may comprise one or more cutting blades mounted in an angle and configured to cut and sharpen pencil tips. It is understood that other arrangements of blades may be used to sharpen pencil tips and to create conical tips as desired, as would be known by a person of ordinary skill. In one aspect, sharpener assembly 114 may also include a motor 118 for rotating cutting blades of the sharpener assembly 114. If utilized, a user may sharpen a pencil by simply inserting the pencil into the appropriate opening 108 to initiate activation of motor 118 and automation of cutting blades of the sharpener assembly 114. Coupling of the cutting blades of sharpener assembly 114 to motor 118 may be accomplished via direct coupling of the motor 118 to the sharpener assembly 114, indirect coupling via gears, or other means as would be known by a person of ordinary skill in the art.

Figure 4B:
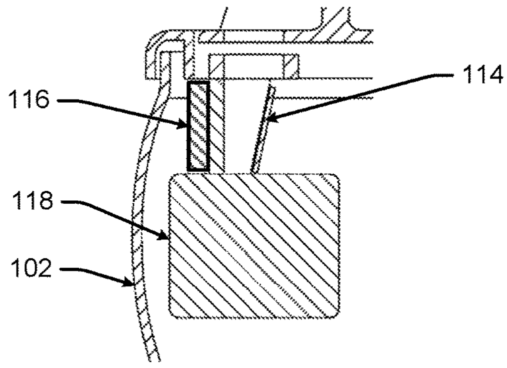
FIG. 4B illustrates a detailed section view of a pencil sharpener with an integrated heating element, in accordance with various aspects of the subject technology.
Figure 4C:
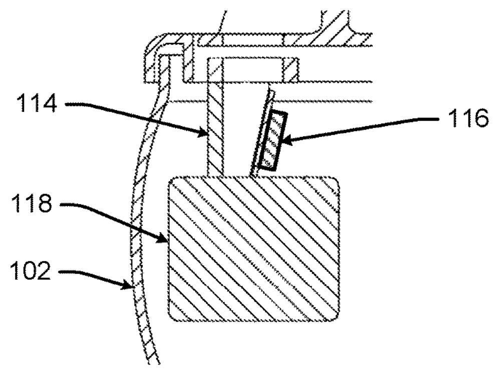
FIG. 4C illustrates a detailed section view of a pencil sharpener with an integrated heating element, in accordance with various aspects of the subject technology.

Heating element 116 may be thermally coupled to sharpener assembly 114 to heat a pencil tip during sharpening. Heating element 116 may convert electricity into heat through resistive heating where electricity entering the element 116 encounters resistance thereby heating the element 116. In some aspects, the heating element 116 may comprise a metallic alloy such as Nichrome, Kanthal, Cupronickel, wire, ribbon or a strip, a ceramic such as molybdenum disilicide or other similar material, composite, or polymer. In some aspects, the desired temperature for heating element 116 may range between 100-3500 degrees Fahrenheit, depending on the pencil and/or cosmetic composition. As shown in FIG. 4A, the heating element 116 may be disposed at an end of the sharpener assembly 114, closest to a pencil tip, and configured to heat the sharpener assembly through heat conduction, that is through the transfer of heat from the heating element 116 to the sharpener assembly 114. In this regard, use of a thermal interface material, such as a thermal filler or putty may be used to maximize heat transfer. In another aspect, the heating element 116 may be disposed along a side of the sharpener assembly 114, as shown in FIG. 4B. As discussed above, in this configuration, the use of a thermal interface material may also be used to increase the efficiency of heat transfer from the heating element 116 to the sharpener assembly 114. In yet another aspect, the heating element 116 may be disposed on a cutting blade as shown in FIG. 4C. In this configuration, heat transfer from the heating element 116 to a tip of a pencil may be optimized as the cutting blade comes into direct contact with the tip of a pencil. It is understood that other means of heating a tip of a pencil may be utilized and are included within the scope of the invention, such as utilizing a cutting blade that is itself a heating element, use of a heating element that utilizes radiation, radiation and conduction, or other heating methods, as would be understood by a person of ordinary skill. In other aspects, the desired temperature for heating element 116 may be adjusted by the user.

Referring back to FIG. 4A, sharpener 100 may also include a separate heating element 112 configured to receive a tip of a pencil. As discussed above, heating element 112 may convert electricity into heat through resistive heating where electricity entering the element 112 encounters resistance thereby heating the element 112. The interior surface of heating element 112 may have a conical shape that corresponds to a tip of a pencil. If utilized, a user may simply insert a pencil into the appropriate opening 108 to heat the tip of the pencil as desired.

Figure 5:
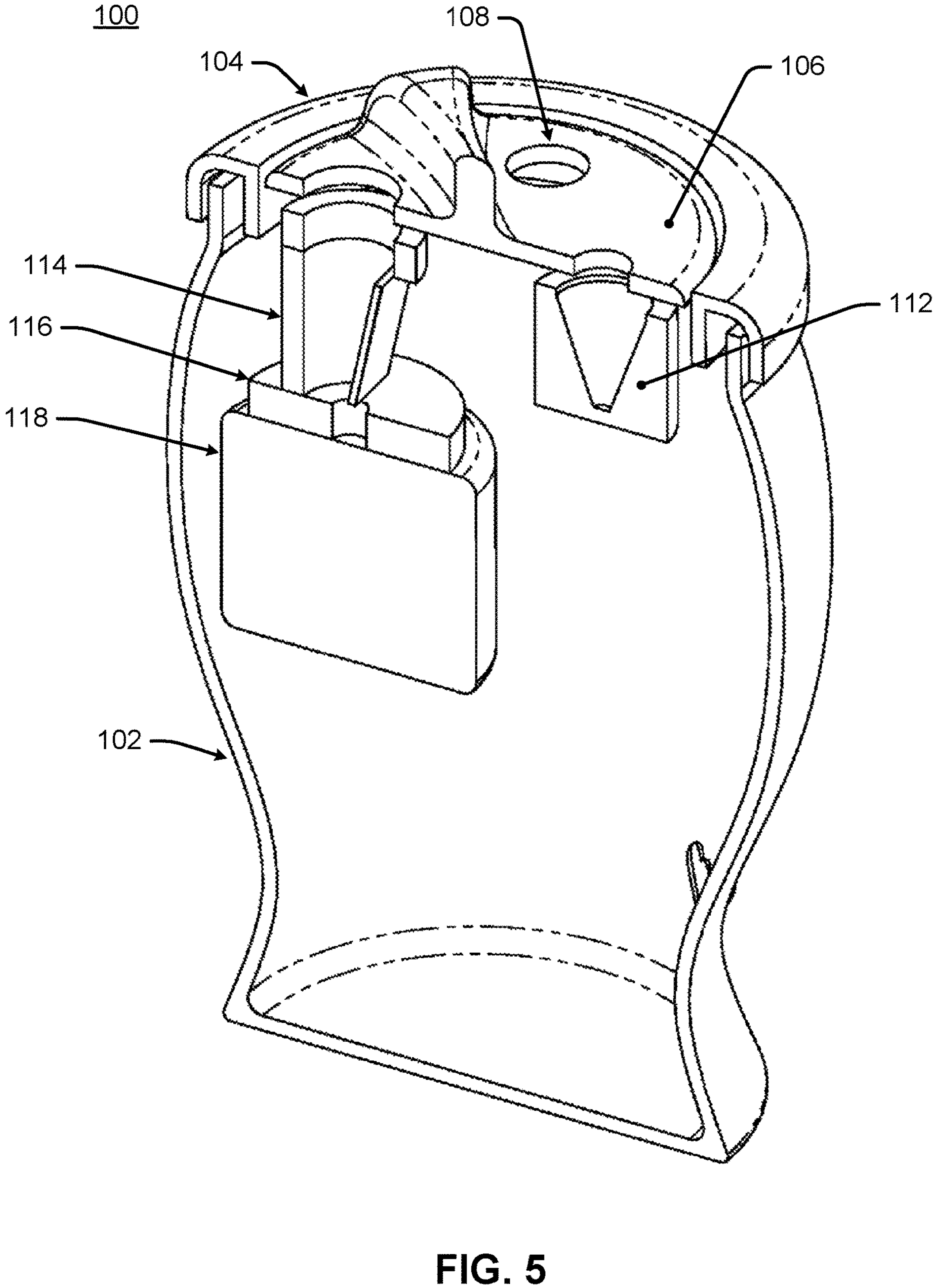
FIG. 5 illustrates a perspective section view of a pencil sharpener with an integrated heating element, in accordance with various aspects of the subject technology.

Referring to FIG. 5 a perspective section view of the sharpener 100 is illustrated. As discussed above, sharpener 100 may comprise a base 102, removable lid 104, rotatable dial 106 having one or more varying openings 108 configured to receive a pencil, dedicated heating element 112, sharpener assembly 114 having an integrated heating element 116, and motor 118 for actuating sharpener assembly 114.

Figure 6A:
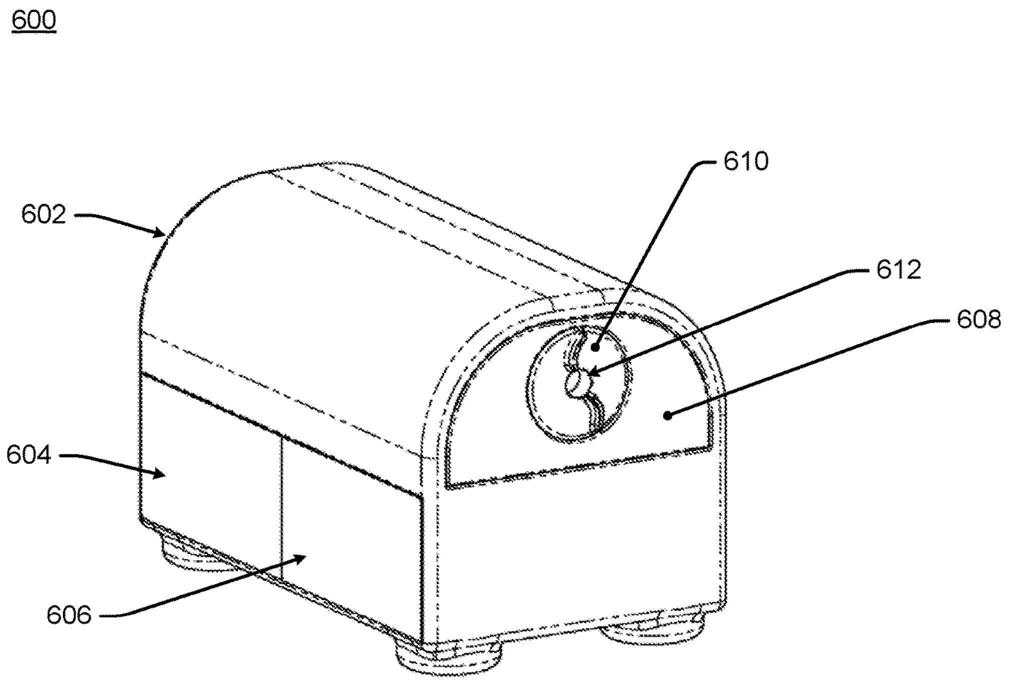
FIG. 6A illustrates a perspective section view of a pencil sharpener with an integrated heating and sanitation element, in accordance with various aspects of the subject technology.

FIG. 6A illustrates a perspective section view of a pencil sharpener 600 with an integrated heating and sanitation element, in accordance with various aspects of the subject technology. Pencil sharpener 600 may comprise a housing 602 and removable cartridge 608. The housing 602 may include one or more drawers 604 for storing components of the pencil sharpener 600. For example, drawer 604 may be configured to slide in and out of housing 602 to provide an area for storing interchangeable disks 610 having differing sized openings 612 for accepting different sized pencils (as discussed above with reference to openings 108). The housing 602 may further comprise a debris drawer 606 for capturing pencil shavings created by operation of the pencil sharpener.

Figure 6B:
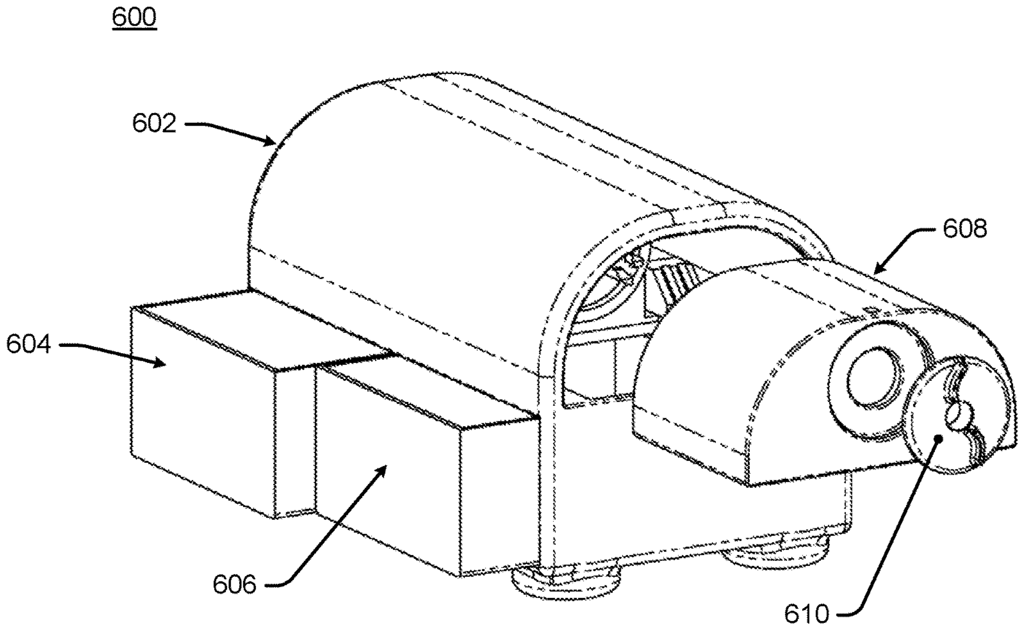
FIG. 6B illustrates an exploded perspective section view of a pencil sharpener with an integrated heating and sanitation element, in accordance with various aspects of the subject technology.
Figure 7:
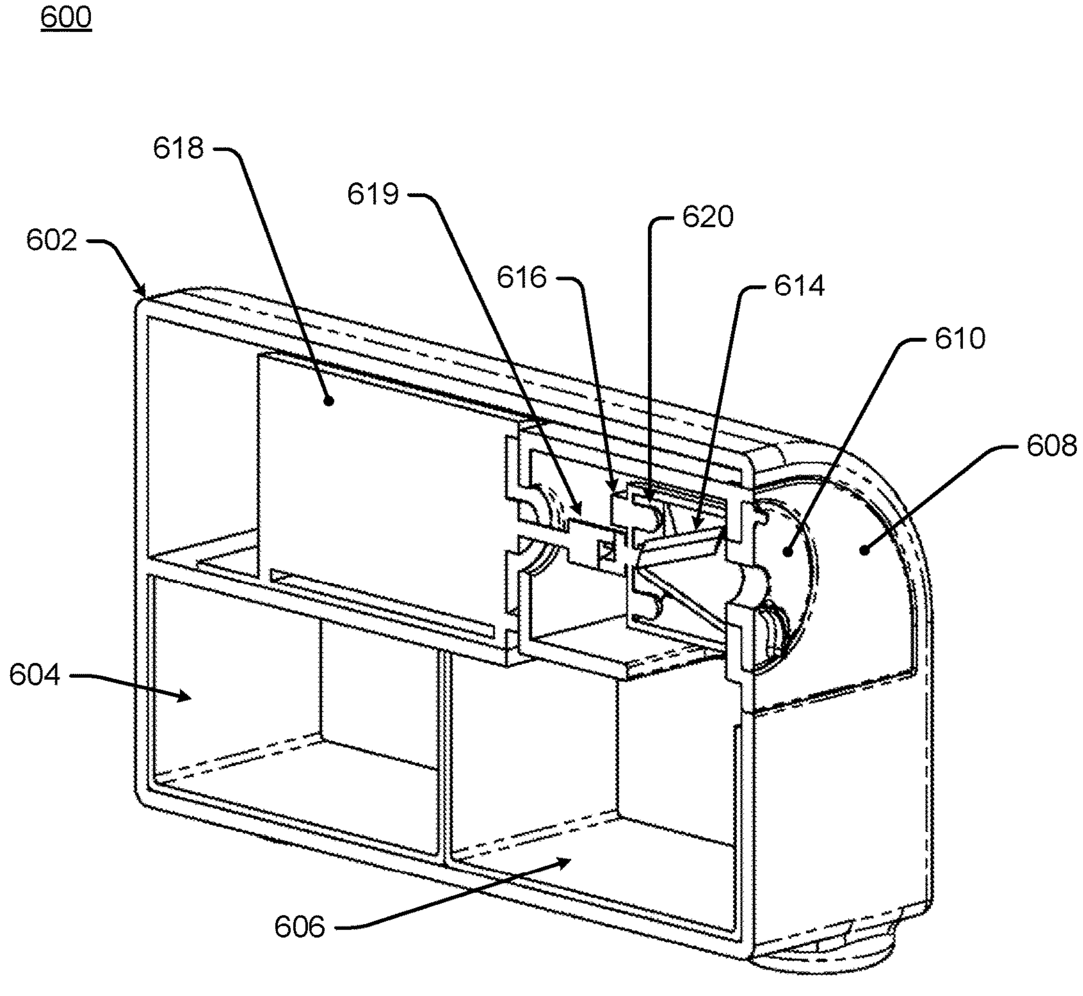
FIG. 7 illustrates a section view of a pencil sharpener with an integrated heating and sanitation element, in accordance with various aspects of the subject technology.

FIG. 6B illustrates an exploded perspective section view of the pencil sharpener 600 with an integrated heating and sanitation element, in accordance with various aspects of the subject technology. Storage drawer 604 and debris drawer 606 are each shown in an open configuration. Similarly, removable cartridge 608 is depicted in a removed configuration with interchangeable disk 610 also shown in a disassembled configuration. In one aspect the removable cartridge 608 is configured to be easily removed from the housing 602 to allow cleaning of cutting blade(s) or other sharpener components (as shown in FIG. 7). The removable cartridge may be composed of a rigid polymer, metal alloy, or other similar material that may be used to house sharpener components and electronics. In another aspect, the removable cartridge may have geometry to restrict insertion into the housing 602 in only one direction or orientation. For example, the removable cartridge 608 may comprise a half-circular shape to encourage the user to insert the cartridge 608 into the housing 602 in the correct orientation.

In one aspect, the interchangeable disk 610 may be configured to slide into a corresponding opening or recess disposed on the removable cartridge 608 to secure the interchangeable disk 610 to the removable cartridge 608. In another example, the interchangeable disk 610 may be configured to engage a threaded opening disposed on the removable cartridge 608. Other mechanical methods for attaching the interchangeable disk 610 to the removable cartridge are contemplated without departing from the scope of the invention.

FIG. 7 illustrates a section view of the pencil sharpener 600 with an integrated heating and sanitation element, in accordance with various aspects of the subject technology. The pencil sharpener 600 may comprise a motor 618 coupled to the removable cartridge 608 via a coupling 619. In one aspect, the motor may be fixed to the housing 602. The motor 618 may comprise an electric motor that either directly or indirectly drives a cutting blade of a sharpener assembly 614. In one aspect, the coupling 619 may be configured to receive the removable cartridge 608 with a self-aligning mechanical coupling. For example, the coupling 619 may comprise a plurality of teeth having chamfered edges that are configured to engage a corresponding coupling disposed on the removable cartridge 608. The coupling disposed removable cartridge 608 may cause one or more cutting blades of the sharpener assembly 614 to rotate as the coupling is rotated by the motor 618.

The removable cartridge 608 may further comprise the sharpener assembly 614, heating element 616 and sanitation element 620. The sharpener assembly 614 may be entirely enclosed by the removable cartridge 608. To allow shavings created by the sharpener assembly 614 to be captured by debris drawer 606, the removable cartridge 608 may have an opening disposed between the sharpener assembly 614 and debris drawer 606 to allow shavings to pass through to the debris drawer 606.

The heating element 616 may comprise similar materials and operate similarly as described above with respect to heating element 116. As shown in FIG. 7, the heating element may be disposed within the removable cartridge 608 and may be configured to heat an end of a pencil as it is sharpened by sharpener assembly 614. The removable cartridge 608 may further comprise one or more sanitation elements 620 to disinfect material comprising the tip of the pencil. Sanitation element 620 may comprise one or more ultraviolet light emitting diodes ("LED") that are each configured to illuminate when the pencil sharpener 600 is in operation. The ultraviolet LED lamps may be configured to emit UV light at selectable wavelengths between 255 and 280 nm to kill or inactivate microorganisms, such as bacteria, viruses, molds and other pathogens, by destroying nucleic acids and disrupting their DNA.

Figure 8:
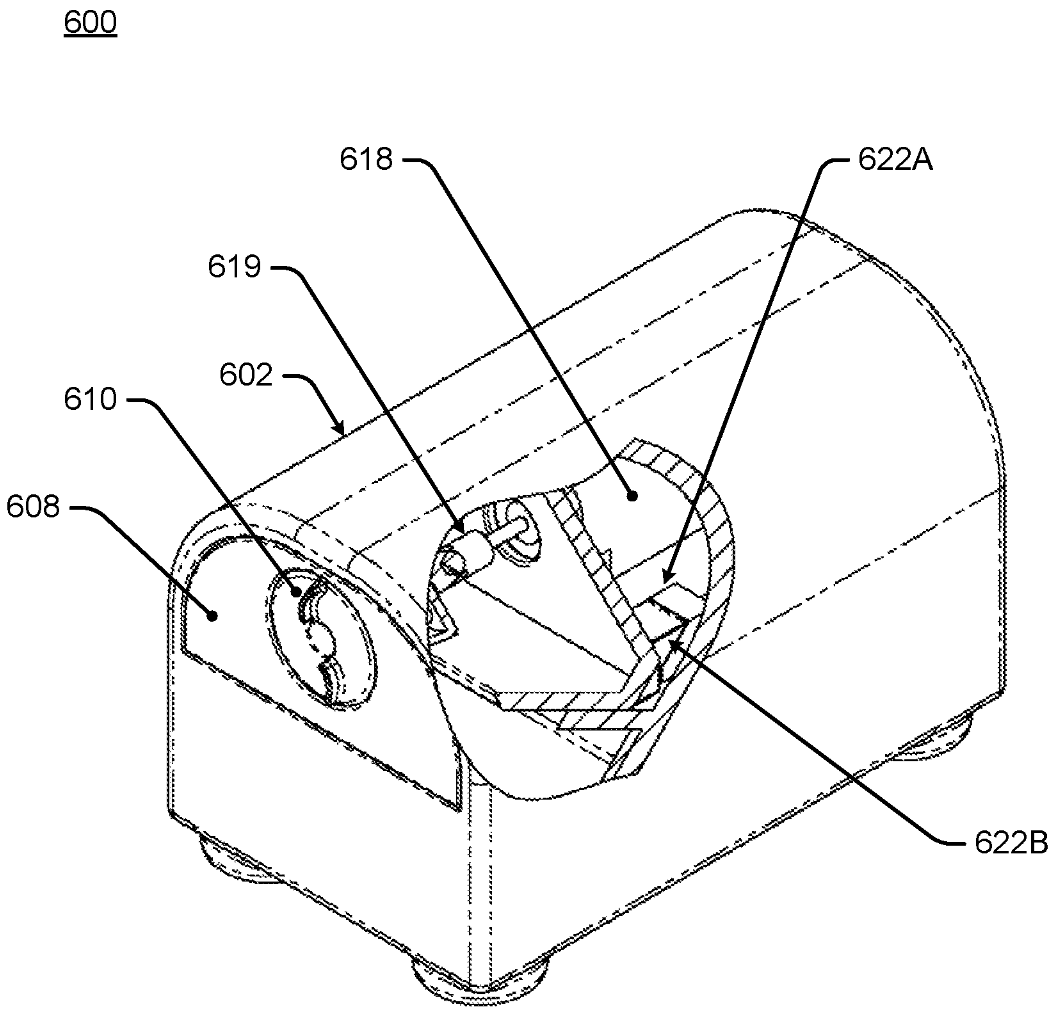
FIG. 8 illustrates a partial section view of a pencil sharpener with an integrated heating and sanitation element, in accordance with various aspects of the subject technology.

FIG. 8 illustrates a partial section view of the pencil sharpener 600, in accordance with various aspects of the subject technology. In one aspect, an electrical connector 622A may be disposed within housing 602 of the pencil sharpener 600. The electrical connector 622A may include spring loaded conductors that are configured to engage a corresponding set of conductors 622B disposed on the removable cartridge 608. Upon insertion of the removable cartridge 608 into the housing 602, the conductors 622B and 622A come into contact with each other thereby providing power to the removable cartridge 608 components, including the heating element 616 and sanitation elements 620.

A method for heating an end of a pencil will now be described. The method involves inserting an end of a pencil in a housing, sharpening the end of the pencil with a blade disposed within the housing, and heating the end of the pencil with a heating element disposed within the housing. The method may further include charging a rechargeable battery disposed within the housing. In one aspect, the rechargeable battery may be electrically coupled to the heating element, sanitation element, and if motorized, to the sharpener assembly. The method may further comprise viewing an indicator that is configured to provide feedback regarding a status of the heating element, as described above.

The description of the subject technology is provided to enable any person skilled in the art to practice the various embodiments described herein. While the subject technology has been particularly described with reference to the various figures and embodiments, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these embodiments will be readily apparent to those skilled in the art, and generic principles defined herein may be applied to other embodiments. Thus, many changes and modifications may be made to the subject technology, by one having ordinary skill in the art, without departing from the scope of the subject technology.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A pencil sharpener comprising:
- a housing;
- a sharpening assembly disposed within the housing, the sharpener assembly comprises a blade and is configured to sharpen an end of a pencil; and
- a heating element disposed within the housing, the heating element coupled to the sharpener assembly and configured to heat the end of the pencil.

2. The pencil sharpener of claim 1, wherein the sharpener assembly comprises a conical support.

3. The pencil sharpener of claim 2, wherein the heating element is coupled to the conical support.

4. The pencil sharpener of claim 1, wherein the heating element is thermally coupled to the sharpening assembly.

5. The pencil sharpener of claim 1, further comprising a motor coupled to the sharpener assembly.

6. The pencil sharpener of claim 1, further comprising a rechargeable battery, wherein the rechargeable battery is electrically coupled to the heating element.

7. The pencil sharpener of claim 1, further comprising an indicator, wherein the indicator is configured to provide feedback to a user of the status of the heating element.

8. The pencil sharpener of claim 1, further comprising a sanitation element, wherein the sanitation element is configured to destroy microorganisms.

9. The pencil sharpener of claim 1, further comprising a dial, wherein the dial comprises a plurality of openings, the openings having at least two or more different diameters.

10. The pencil sharpener of claim 1, further comprising a secondary heating element disposed away from the sharpener assembly.

11. A pencil sharpener comprising:
- a housing;
- a removable cartridge, the removable cartridge having a recess and comprising a sharpening assembly, a heating element, and a sanitation element; and
- wherein the sharpening assembly comprises a blade and is configured to sharpen an end of a pencil;
- wherein the heating element is coupled to the sharpener assembly and configured to heat the end of the pencil; and
- wherein the sanitation element is configured to destroy microorganisms located at the end of the pencil;
- a plurality of disks, wherein each disk of the plurality of disks has an opening having a diameter for receiving an end of the pencil, wherein the diameter of each disk of the plurality of disks is different from the diameter of the other disks of the plurality of disks, and wherein each disk of the plurality of disks is configured to engage the recess of the removable cartridge;
- a storage compartment disposed within the housing for storing the plurality of disks.

12. The pencil sharpener of claim 11, wherein the sharpener assembly comprises a conical support.

13. The pencil sharpener of claim 11, wherein the heating element is thermally coupled to the sharpening assembly.

14. The pencil sharpener of claim 11, further comprising a motor disposed within the housing, wherein the motor is configured to couple to the removable cartridge via a mechanical coupling.

15. The pencil sharpener of claim 11, further comprising a rechargeable battery, wherein the rechargeable battery is electrically coupled to the heating element and the sanitation element.

16. The pencil sharpener of claim 11, further comprising an indicator, wherein the indicator is configured to provide feedback to a user of the status of the heating element.

17. A method for heating an end of a pencil, the method comprising;
- inserting an end of a pencil in a housing;
- sharpening the end of the pencil with a blade disposed within the housing; and
- heating the end of the pencil with a heating element disposed within the housing.

18. The method of claim 17, wherein the heating element is thermally coupled to the blade.

19. The method of claim 17, further comprising charging a rechargeable battery disposed within the housing, wherein the rechargeable battery is electrically coupled to the heating element.

20. The method of claim 17, further comprising viewing an indicator, wherein the indicator is configured to provide feedback regarding a status of the heating element.

* * * * *